United States Patent
Cai et al.

(10) Patent No.: US 9,897,566 B2
(45) Date of Patent: Feb. 20, 2018

(54) DISPOSABLE TEST SENSOR

(71) Applicants: Xiaohua Cai, Changsha (CN); Hongli Che, Changsha (CN); Shaobo Li, Changsha (CN)

(72) Inventors: Xiaohua Cai, Changsha (CN); Hongli Che, Changsha (CN); Shaobo Li, Changsha (CN)

(73) Assignee: Changsha Sinocare Inc., Hi-Tech Zone, Changsha, Hunan (CN)

( * ) Notice: Subject to any disclaimer, the term of this patent is extended or adjusted under 35 U.S.C. 154(b) by 643 days.

(21) Appl. No.: 14/153,654

(22) Filed: Jan. 13, 2014

(65) Prior Publication Data

US 2015/0198554 A1    Jul. 16, 2015

(51) Int. Cl.
*G01N 27/327*    (2006.01)

(52) U.S. Cl.
CPC .................. *G01N 27/3272* (2013.01)

(58) Field of Classification Search
USPC .................................................... 204/403.01
See application file for complete search history.

(56) References Cited

U.S. PATENT DOCUMENTS

| | | |
|---|---|---|
| 4,431,507 A | 2/1984 | Nankai et al. |
| 4,498,968 A | 2/1985 | Yamada et al. |
| 4,534,356 A | 8/1985 | Papadakis |
| 5,102,525 A | 4/1992 | Miyahara et al. |
| 5,120,420 A | 6/1992 | Nankai et al. |
| 5,126,034 A | 6/1992 | Carter et al. |
| 5,128,012 A | 7/1992 | Szuminsky et al. |
| 5,128,015 A | 7/1992 | Szuminsky et al. |
| 5,138,521 A | 8/1992 | Koshishi |

(Continued)

FOREIGN PATENT DOCUMENTS

| | | |
|---|---|---|
| CN | 94205849.6 | 6/1996 |
| CN | 99249332.3 | 8/2000 |

(Continued)

OTHER PUBLICATIONS

USPTO Office Action—U.S. Appl. No. 13/890,303, dated Oct. 20, 2015.

(Continued)

*Primary Examiner* — Jill Warden
*Assistant Examiner* — Julie Tavares
(74) *Attorney, Agent, or Firm* — Lambert & Associates; Gary E. Lambert; David J. Connaughton, Jr.

(57) ABSTRACT

The present invention relates to disposable test sensors having improved sample application and measuring properties and their uses for detection, preferably, quantitative measurement, of analyte in a liquid sample like blood. In particular, the invention provides for an electrochemical biosensor which has a thin-layer fluid chamber having funnel-like shape with a novel extra wide opening as sampling entrance and a vent opening at the tip of the chamber for air escape. The thin-layer fluid chamber provides a reservoir from which a sample fluid can be drawn into it through capillary action. The extra wide sampling entrance provided by the present invention can draw blood into the chamber through any part of the opening, thus it allows easy targeting the samples with small volume, picking up smeared samples and it is more tolerant to users who jam the tip of the sensor into users' finger.

18 Claims, 7 Drawing Sheets

(56) References Cited

U.S. PATENT DOCUMENTS

| | | |
|---|---|---|
| 5,264,103 A | 11/1993 | Yoshioka et al. |
| 5,344,545 A | 9/1994 | Tsukada et al. |
| 5,437,999 A | 8/1995 | Diebold et al. |
| 5,575,895 A | 11/1996 | Ikeda et al. |
| 5,582,697 A | 12/1996 | Ikeda et al. |
| 5,665,222 A | 9/1997 | Heller et al. |
| 5,708,247 A | 1/1998 | McAleer et al. |
| 5,739,039 A | 4/1998 | Hugues |
| 5,762,770 A | 6/1998 | Pritchard et al. |
| 5,858,201 A | 1/1999 | Otsuka et al. |
| 5,975,153 A | 11/1999 | Hill et al. |
| 6,004,441 A | 12/1999 | Fujiwara et al. |
| 6,071,391 A | 6/2000 | Gotoh et al. |
| 6,125,292 A | 9/2000 | Uenoyama et al. |
| 6,287,451 B1 | 9/2001 | Winarta et al. |
| 6,428,664 B1 | 8/2002 | Bhullar et al. |
| 6,540,891 B1 | 4/2003 | Stewart et al. |
| 6,592,746 B1 | 7/2003 | Feldman et al. |
| 6,645,359 B1 | 11/2003 | Bhullar et al. |
| 6,767,440 B1 | 7/2004 | Bhullar et al. |
| 6,767,441 B1 | 7/2004 | Cai et al. |
| 6,787,013 B2 | 9/2004 | Chang et al. |
| 6,793,802 B2 | 9/2004 | Lee et al. |
| 6,803,205 B2 | 10/2004 | Duffy et al. |
| 6,923,894 B2 | 8/2005 | Huang et al. |
| 6,942,770 B2 | 9/2005 | Cai et al. |
| 7,063,776 B2 | 6/2006 | Huang |
| 7,073,246 B2 | 7/2006 | Bhullar et al. |
| 7,118,667 B2 | 10/2006 | Lee |
| 7,276,146 B2 | 10/2007 | Wilsey |
| 7,288,174 B2 | 10/2007 | Cui et al. |
| 7,297,248 B2 | 11/2007 | Bae et al. |
| 7,386,937 B2 | 6/2008 | Bhullar et al. |
| 7,547,383 B2 | 6/2009 | Cai et al. |
| 7,641,785 B2 | 1/2010 | Shinno et al. |
| RE41,264 E | 4/2010 | Cai et al. |
| 7,740,746 B2 | 6/2010 | Huang |
| 7,802,467 B2 | 9/2010 | Wang |
| 7,824,616 B2 | 11/2010 | Katsuki et al. |
| 7,955,484 B2 | 6/2011 | Cai et al. |
| RE42,567 E | 7/2011 | Hodges et al. |
| RE42,953 E | 11/2011 | Crismore et al. |
| 8,071,030 B2 | 12/2011 | Bhular et al. |
| 8,088,271 B2 | 1/2012 | Fujiwara et al. |
| 8,128,981 B2 | 3/2012 | Popovich et al. |
| 8,142,629 B2 | 3/2012 | Miyazaki et al. |
| 8,211,379 B2 | 7/2012 | Burke et al. |
| 8,222,044 B2 | 7/2012 | Bhullar et al. |
| 8,287,703 B2 | 10/2012 | Bhullar et al. |
| RE43,815 E | 11/2012 | Crismore et al. |
| 8,303,801 B2 | 11/2012 | Wilsey |
| 8,241,486 B2 | 12/2012 | Petyt et al. |
| 8,323,464 B2 | 12/2012 | Pugh et al. |
| 8,377,378 B2 | 2/2013 | Feldman et al. |
| 8,414,761 B2 | 4/2013 | Gotoh et al. |
| 8,414,762 B2 | 4/2013 | Petyt et al. |
| 8,430,999 B2 | 4/2013 | Onoda et al. |
| 8,480,869 B2 | 7/2013 | Fujiwara et al. |
| 8,506,775 B2 | 8/2013 | Surridge et al. |
| 8,511,147 B2 | 9/2013 | Wang |
| 8,535,497 B2 | 9/2013 | Fujiwara et al. |
| 8,540,864 B2 | 9/2013 | Fujiwara et al. |
| 8,551,308 B2 | 10/2013 | Bhullar et al. |
| 8,679,309 B2 | 3/2014 | Beer et al. |
| 2001/0034068 A1 | 10/2001 | Spivey et al. |
| 2004/0050717 A1 | 3/2004 | Teodorczyk et al. |
| 2005/0145490 A1 | 7/2005 | Shinno et al. |
| 2005/0214171 A1 | 9/2005 | Gerstle et al. |
| 2005/0269214 A1 | 12/2005 | Lee |
| 2005/0277850 A1 | 12/2005 | Mace et al. |
| 2006/0272958 A1 | 12/2006 | Lee et al. |
| 2007/0131548 A1 | 6/2007 | Winarta et al. |
| 2007/0235347 A1 | 10/2007 | Chatelier et al. |
| 2008/0006530 A1 | 1/2008 | Winarta et al. |
| 2008/0128278 A1 | 6/2008 | Bae et al. |
| 2008/0148873 A1 | 6/2008 | Wang |
| 2009/0078030 A1 | 3/2009 | Jung |
| 2009/0157001 A1 | 6/2009 | Jones |
| 2009/0215159 A1 | 8/2009 | Kirby |
| 2011/0048940 A1* | 3/2011 | Wang ................ G01N 27/3272 204/403.14 |
| 2011/0174613 A1 | 7/2011 | Miyazaki et al. |
| 2012/0009095 A1 | 1/2012 | Burke et al. |
| 2012/0055626 A1 | 3/2012 | Bhullar et al. |
| 2012/0174688 A1 | 7/2012 | Calasso et al. |
| 2012/0186996 A1 | 7/2012 | Wilsey et al. |
| 2012/0234487 A1 | 9/2012 | Wang |
| 2013/0027064 A1 | 1/2013 | Austera et al. |
| 2013/0032284 A1 | 2/2013 | Petyt et al. |
| 2013/0062221 A1 | 3/2013 | Cai et al. |
| 2013/0306472 A1 | 11/2013 | Kaneda et al. |
| 2013/0341208 A1 | 12/2013 | Whyte et al. |
| 2014/0021046 A1 | 1/2014 | Huang et al. |
| 2014/0054171 A1 | 2/2014 | Feldman et al. |
| 2014/0147912 A1 | 5/2014 | Cho et al. |
| 2014/0158553 A1 | 6/2014 | Fujiwara et al. |
| 2014/0174922 A1 | 6/2014 | Beer et al. |
| 2014/0262773 A1 | 9/2014 | Riggles et al. |

FOREIGN PATENT DOCUMENTS

| | | |
|---|---|---|
| CN | 99119827.1 | 7/2001 |
| CN | 02111330.0 | 10/2002 |
| CN | 03116172.3 | 10/2003 |
| CN | 03117061.7 | 2/2004 |
| CN | 02139888.7 | 7/2004 |
| CN | 200420091585.4 | 12/2005 |
| CN | 200520017197.6 | 6/2006 |
| CN | 200610088404.6 | 2/2007 |
| CN | 200710178643.5 | 4/2008 |
| CN | 200710040500.8 | 11/2008 |
| JP | 2000162176 | 6/2000 |
| WO | WO 2013117924 | 8/2013 |
| WO | WO 2013190072 | 12/2013 |
| WO | WO 2014140161 | 9/2014 |

OTHER PUBLICATIONS

USPTO Office Action—U.S. Appl. No. 14/099,418, dated Mar. 23, 2016.

USPTO Office Action—U.S. Appl. No. 14/184,764, dated Jul. 1, 2016.

Patent Cooperation Treaty International Search Report—WO2015126456-ISR-010, dated Dec. 22, 2014.

Patent Cooperation Treaty International Search Report—WO2015084448, dated Dec. 22, 2014.

Patent Cooperation Treaty International Search Report—WO2015105536, dated Dec. 22, 2014.

* cited by examiner

DISPOSABLE TEST SENSOR

FIELD OF THE INVENTION

The present invention generally relates to a test sensor or strip. More specifically, the present invention generally relates to a disposable biosensor with a thin-layer fluid chamber that is adapted to receive a fluid sample around with small volume. Still more specifically, the present invention generally relates an electrochemical biosensor with an extra wide sampling entrance. Still more specifically, the present invention relates methods of making and using the biosensors.

BACKGROUND OF THE INVENTION

The use of disposable test sensors such as strips in the medical field for testing various analytes in body fluid is well known. The accurate determination of analytes in body fluids is of great importance in the diagnoses of certain physiological abnormalities. In particular, it is important that diabetic individuals frequently check their glucose level in their body fluids to regulate the glucose intake in their daily diets. The results of such tests can be used to determine the insulin dosage or other medication needs to be administered. In one type of blood-glucose testing system, test sensors, or called glucose strips, are used by diabetic individuals to test a sample of blood in connection with a hand-held meter. The glucose strips are used by millions of diabetics throughout the world on a daily base.

There are hundreds of brand names of glucose strips in the market. They are very similar in terms of sensor construction: i.e., a channel is formed between a generally U-shaped spacer and is adapted to receive blood from the opening end of the sensor through capillary action and escape air from the other end through an air escape vent. In order to reduce blood volume, thus reduce pain from piercing finger or other sampling points, the blood receiving chamber is usually small and, as a result, the sampling entrance is also relatively small. As the volume of fluid chambers in the sensors decreases, it becomes increasingly more difficult to fill the fluid chamber with the sample to be analyzed. It has been observed that users may abuse the test sensor by jamming the tip of the test sensor into the individual's finger, which very probably results in incomplete blood filling, non-continuous filling or wiggling of blood flow. Additionally, in some existing test sensors, it is difficult to position the fluid sample within the channel entrance opening especially for those diabetics who have poor vision and/or trembling hand. Besides, blood samples turn to smear around the tip of fingers or other sampling points. It becomes very difficult to draw such smeared blood into the sensor chamber. All of these phenomena may eventually lead to biased readings, and as a result, wrong dosage of insulin administration and even life threatening errors may occur.

Therefore, in order to reduce or eliminate such biased readings caused by such user action and/or reduce the difficulty in connection with sampling, it would be highly desirable to have a more user friendly test sensor that could easily target sample, easily draw sample into the sensor chamber, and alleviate incomplete filling, non-continuous filling and other issues that may result in inaccurate test results. The present disclosure is directed to a novel design and method to overcome one or more of the limitations in the prior arts.

SUMMARY OF THE INVENTION

According to the first embodiment, a disposable electrochemical test sensor has a funnel-like chamber having a novel extra wide sampling entrance and a vent opening at the tip of the chamber for air escape. Such a design is adapted to improve sampling of fluid samples. The fluid chamber provides a thin-layer reservoir from which sample fluid can be drawn into the funnel-like chamber through capillary action. The extra wide sampling entrance provided by the present invention can draw blood into the chamber through any part of the opening end. Thus it allows easily targeting the samples with small volume, picking up smeared samples and alleviating jamming the opening end. In preferred embodiments, the sensor consists of multiple layers which include a base layer having conductive coatings serving as working and reference electrodes; a middle layer having funnel-like shape serving as spacer; and an upper layer with a hydrophilic surface facing to the chamber. The upper, middle and base layers are laminated through adhesives or other ways to bond each other, such that the thin-layer fluid chamber is formed between a portion of the lower layer surface and the upper layer surface at one end of the sensor, while the other end of the sensor having conductive layer exposed serve as electric contacts in connection with a monitor or meter.

According to the second embodiment, a disposable electrochemical test sensor has a funnel-like chamber having a novel extra wide sampling entrance and a vent opening at the tip of the chamber for air escape. Such a design is adapted to improve sampling of fluid samples. The fluid chamber provides a thin-layer reservoir from which sample fluid can be drawn into the sample receiving chamber through capillary action. The extra wide sampling entrance provided by the present invention can not only draw blood into the fluid chamber through any part of the front opening end, but can also draw blood into the fluid chamber through part of left side and part of right side near the opening end. The front opening and both side openings form a large opening, serving as blood sample entrance. Thus such unique design allows easily targeting the samples with small volume, picking up smeared samples and alleviating jamming of the opening by users' finger. In preferred embodiments, the test sensor consists of multiple layers which include a base layer having conductive coatings serving as working and reference electrodes; a middle layer having funnel-like shape serving as spacer; and an upper layer with a hydrophilic surface facing to the chamber. The upper, middle and base layers are laminated through adhesives or other ways to bond each other, such that the thin-layer fluid chamber is formed between a portion of the lower layer surface and the upper layer surface at one end of the sensor, while the other end of the sensor having conductive layers exposed serve as electric contacts in connection with a monitor or meter.

According to one method, an analyte concentration is measured. A disposable electrochemical test sensor is provided having a funnel-like chamber having a novel extra wide sampling entrance and a vent opening at the tip of the chamber for air escape. The chamber provides a thin-layer reservoir from which sample fluid can be drawn into the thin-layer chamber through capillary action. In preferred embodiments, the sensor consists of multiple layers which include a base layer having conductive coatings serving as working and reference electrodes; a middle layer serves as spacer which may have different shapes, such as circular arc, inverted triangle, inverted trapezoid, funnel-like tapering shape etc.; and an upper layer with a hydrophilic surface facing to the chamber. In preferred embodiments, the middle layer is in funnel-like shape, such that an extra wide sampling entrance is formed. The middle layer also defines the electrode areas once laminated onto the base layer with conductive coating at the surface. The upper, middle and base layers are attached through adhesives or other ways to bond each other, such that the thin-layer fluid chamber is formed between a portion of the lower layer surface and the upper layer surface at one end of the sensor, while the other end of the sensor having conductive layers exposed serve as electric contacts in connection with a monitor or meter.

DETAILED DESCRIPTION OF ILLUSTRATED EMBODIMENTS

The test sensor of the present invention is directed to improve sampling entrance of the strip for the determination of an analyte concentration of in a fluid sample, such as blood. In one embodiment, a test sensor is adapted to receive a fluid sample from one end of the sensor, while the other end is connected with an instrument or meter. Analytes that may be measured include, but not limited to glucose, lactate, uric acid, creatinine, creatine, cholesterol, triglycerides, hemoglobin, bilirubin, alcohol, etc. The fluid sample may be any body fluid, thus, the analytes may be in, for example, a whole blood sample, a blood serum sample, a blood plasma sample, other body fluids like tears, interstitial fluid and urine. In one preferred method, the testing equipment is a hand-held meter.

Figure 1A:
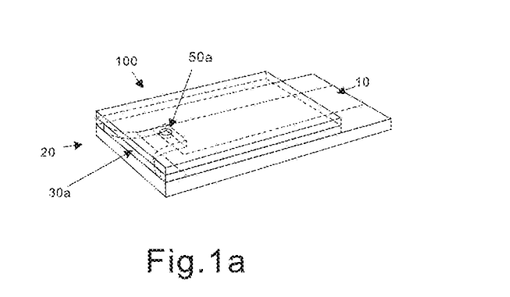
FIGS. 1a and 1b are perspective views of the test sensor of the present invention according to the first (1a) and second (1b) embodiment.
Figure 1B:
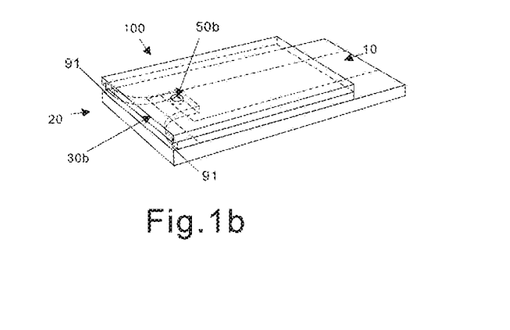

In one embodiment, the test sensor is an electrochemical test sensor. FIGS. 1a and 1b show perspective views of the test sensor of the present invention. The sensor has a sensor body 100, an electric contact end 10 and sampling end 20. The electric contact end may have at least two contacts used for one working electrode and one reference electrode, respectively. The sensor has a thin-layer fluid chamber 30a and a thin-layer fluid chamber 30b, according to the first embodiment and second embodiment, respectively. The thin-layer fluid chambers have funnel-like shape with wide opening as the entrance for fluid sample. Once the fluid sample enters the chamber, the analyte will react with the chemical reagents loaded on the surface of the electrodes, thus resulting in electrochemical signals, which correlate to the concentration of the analytes. Note that the sensor has a vent opening 50a and 50b at the tip of the funnel-like chamber, according to the first embodiment and second embodiment, respectively. The vent openings allow air to escape when the fluid sample enters the chamber.

Figure 2:
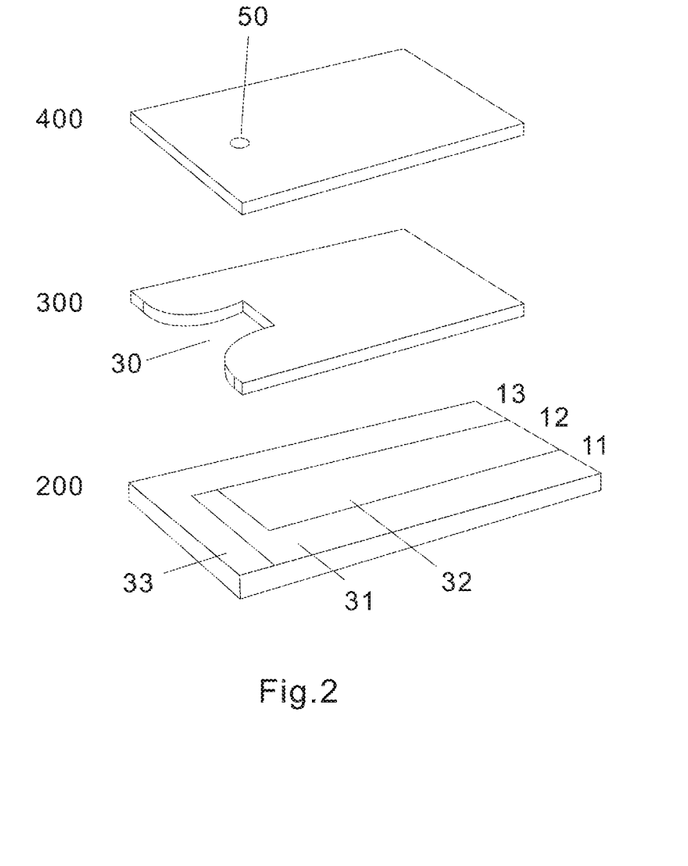
FIG. 2 is an exploded view of the test sensor of the present invention showing the three component layers.

FIG. 2 is an exploded view of the test sensor of the present invention showing the three component layers. In one preferred embodiment, the electric contact end 10 has three electric contacts at the electric contact end, serving as contacts for a first working electrode 11; a second working electrode 13 and a reference electrode 12, respectively. The electric contacts 11, 12, 13 are related to corresponding electrodes at the sampling end 20. In one embodiment, the test sensor consists of multiple layers which include a base layer 200; a middle layer 300; and an upper layer 400, as shown in FIG. 2.

Figure 3A:
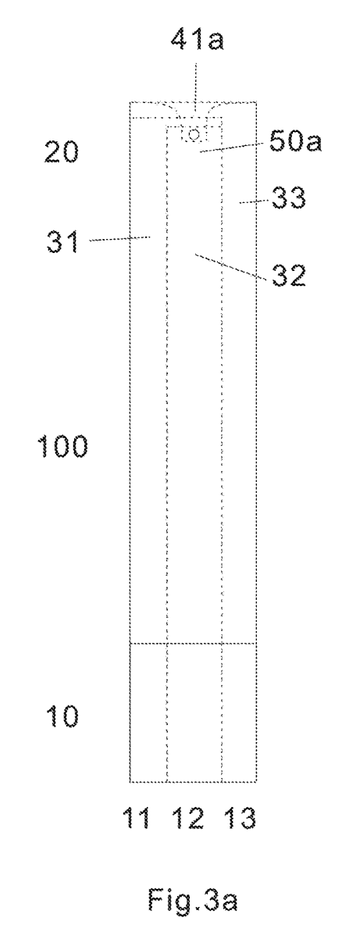
FIGS. 3a and 3b are top views of the test sensor of the present invention consisting of three laminated layers according to the first (3a) and second (3b) embodiment.
Figure 3B:
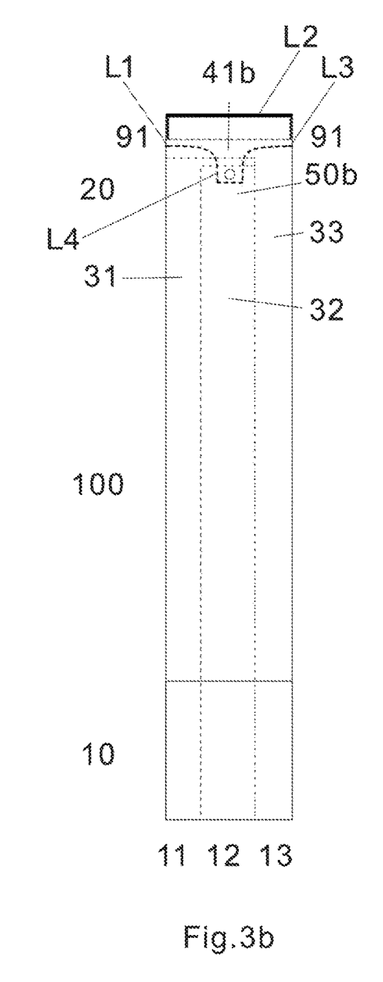

FIGS. 3a and 3b are top views of the test sensor of the present invention consisting of three laminated layers according to the first (3a) and second (3b) embodiment. At the sampling end 20, there are three electrodes, corresponding to the first working electrode 31, second working electrode 33 and reference electrode 32. At electric contact end 10, there are three electric contacts 11, 12 and 13, connecting to the first working electrode 31; reference electrode 32; second working electrode 33; respectively. Note that the arrangement or order of the electrodes is not crucial for the essence of test sensor of the present invention. 91 in FIG. 3b denotes the side opening of the sampling entrance of the biosensor according to the second embodiment in the present invention, which will be discussed in the following sections. As can be seen in FIG. 3b, in this embodiment, the opening has a combined length equal to the open front length L2 (which is the same as the width of the test sensor) and the two side opening lengths L1, L3. A perimeter length L4 (which is the bold broken line) of the middle layer cutout region 41b, which in turn defines a perimeter of the fluid chamber, is defined as a length of the perimeter edge defined by the cutout from one widthwise end of the middle layer to the other widthwise end. In the embodiment shown, the perimeter length L4 is the length of the funnel shaped cutout 41b. The combined length of the opening (L1+L2+L3) is less than the perimeter length L4 of the middle layer cutout region 41b.

Figure 4:
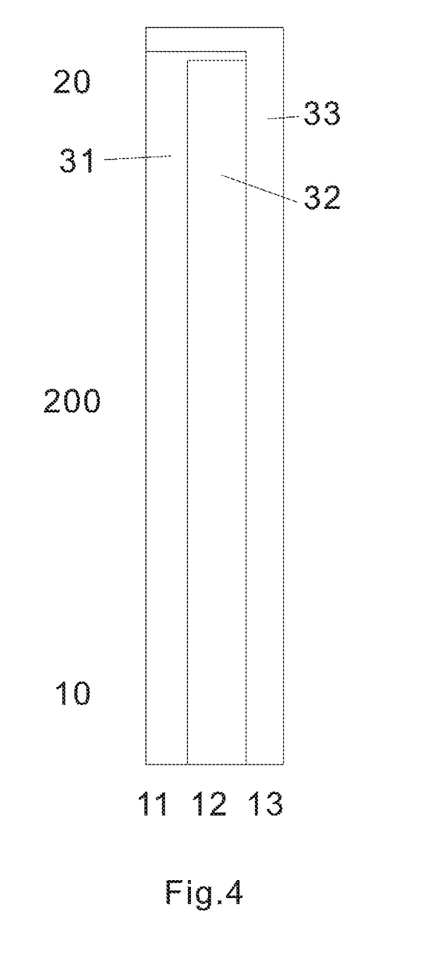
FIG. 4 is a top view of the base layer to be used in forming a test sensor according to one embodiment.

FIG. 4 shows a top view of a first base layer 200 to be used in forming a test sensor according to one embodiment. The base layer 200 may be made from a variety of materials such as polymeric materials, coated with conductive materials such as carbon, various metals or metal oxides. The base layer 200 with conductive coating serves as substrate of the test sensor and chamber forming layer. It also serves as electrodes at one end 20 and electric contacts at the other end 10. Non-limiting examples of polymeric materials, that may be used to form the base layer include, but not limited to polyethylene, polypropylene, polystyrene, polyvinyl chloride, and polytetrafluoroethylene, polycarbonate, polyethylene terephthalate, polyethylene naphthalate, polyimide and combinations thereof. The conductive coating may be formed by a variety of methods which are well known in the field including, but not limited to printing (e.g., screen-printing), coating (e.g., reverse roll), vapor deposition, sputtering, chemical deposition, and electrochemical deposition. The conductive coating may be on a whole piece of insulating material. If so, a desired number of electric conduits must be made. This can be achieved by etching/scribing the required number of conductive conduits. The etching process may be accomplished chemically, by mechanically scribing lines in the conductive layer, or by using a laser to scribe the conductive layer into separate conductive conduits. The conductive materials may be, but not limited to various carbon materials; various noble metals like gold, platinum, palladium, iridium, rhodium, ruthenium; various metal oxides like indium oxide, tin oxide; and combinations thereof.

Figure 5A:
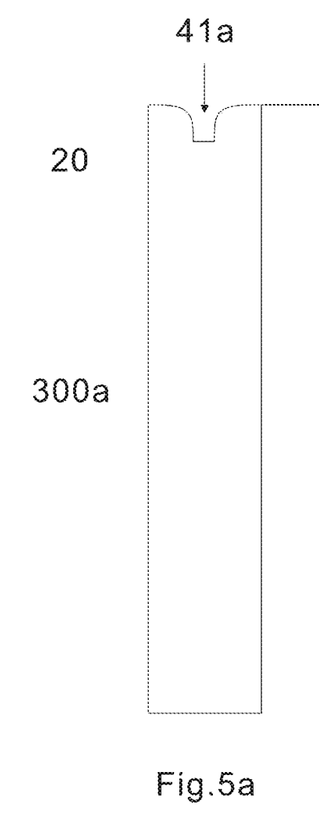
FIGS. 5a and 5b are top views of the middle layer to be used in forming a test sensor according to the first (5a) and second (5b) embodiment.

FIG. 5a shows a top view of the middle layer 300a to be used in forming a test sensor according to the first embodiment. The middle layer 300a virtually has same width as the base layer 200, but shorter in length to leave part of the base layer 300a exposed for electric contacts. The middle layer 300a serves as a spacer in between the base layer 200 and the upper layer 400. The middle layer 300a, or spacer, is also made of a plastic insulating material with glue or adhesive on both sides and creates the thin-layer fluid chamber 30a of the laminated body (FIG. 1a). It contains a funnel-like cutout 41a at the end 20 which overlays the base layer 200 with the open end corresponding to the open end of the laminated body described earlier. The funnel-like cutout 41a has a wide opening with a width of at least 1 mm. The width can be equal or slightly smaller than the width of the base layer 200. More preferably, it is around 2 mm to 20 mm in the present invention. Assuming the test sensor or the component layers (200, 300a and 400) in the present invention have a width of around 6 mm, preferably, the width may be around 5.2 mm. Thus, a blood sample can enter the thin-layer fluid chamber 30a from any part of the entire opening end. A double coated, pressure-sensitive adhesive tape may be used as the middle layer 300a. The cutout 41a creating the thin-layer fluid chamber may have different shapes, including, but not limited to semi-circular, inverted triangle, inverted trapezoid, funnel-like shape and etc. In one preferred embodiment, the cutout is in funnel-like shape. The funnel-like cutout 41a forms a large opening as sampling entrance and also defines electrode areas once laminated onto the base layer 200 with conductive coating at the surface. The thickness and size of the cutout 41a determine the volume of the thin-layer fluid chamber 30a. Preferably, the middle layer 300a has a thickness ranging from 0.01 mm to 0.5 mm. More preferably, the middle layer 300a has a thickness around 0.08 mm in the present invention.

Figure 5B:
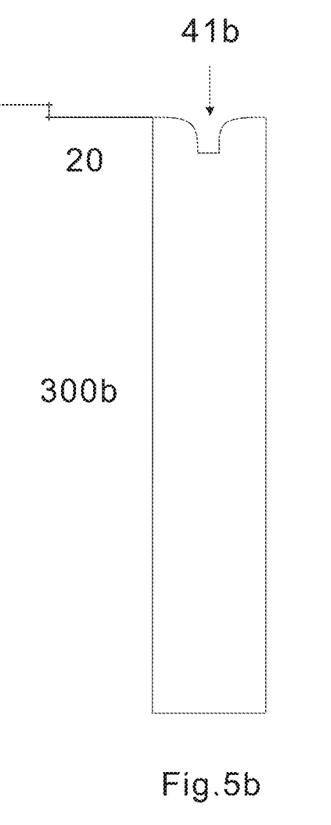

FIG. 5b shows a top view of the middle layer 300b to be used in forming a test sensor according to the second embodiment. The middle layer 300b is alternative to the middle layer 300a according to the first embodiment. The middle layer 300b also serves as a spacer in between the base layer 200 and the upper layer 400. The middle layer 300b virtually has same width as the middle layer 300a, but it is slightly shorter in length at the end 20, as a result, leaving openings at both corners after all three component layers 200, 300b and 400 are laminated. Such a unique design of the present invention forms an over 180° sampling entrance, even wider opening compared to the first embodiment described above. Therefore, a blood sample not only enters the thin-layer fluid chamber 30b from any part of the front opening, but also from both side opening 91 of the test sensor at the end 20, as shown in FIG. 3b. The middle layer 300b, or spacer, is also made of a plastic insulating material with glue or adhesive on both sides and creates the sample fluid chamber of the laminated body. It contains a funnel-like tapering cutout 41b on the end 20 which overlays the base layer 200 with the open end corresponding to the open end of the laminated body described earlier. The funnel-like cutout 41b has a wide opening with a width of at least 1 mm. The width can be equal to or slightly smaller than the width of the base layer 200. More preferably, it is around 2 mm to 20 mm in the present invention. Assuming the test sensor or the component layers (200, 300a and 400) in the present invention have a width of around 6 mm, preferably, the width of funnel-like cutout 41b may be around 5.2 mm. A double coated, pressure-sensitive adhesive tape may be used as the middle layer 300b. The cutout 41b creating the fluid chamber may have different shapes, including, but not limited to semi-circular, inverted triangle, inverted trapezoid, funnel-like shape and etc. In one preferred embodiment, the cutout is in funnel-like shape. The funnel-like cutout 41a forms a large opening as sampling entrance and also defines electrode areas once laminated onto the base layer 200 with conductive coating at the surface. The thickness and size of the cutout 41b determine the volume of the thin-layer fluid chamber 30b. Preferably, the middle layer 300b has a thickness ranging from 0.01 mm to 0.5 mm. More preferably, the middle layer 300b has a thickness around 0.08 mm in the present invention.

Figure 6A:
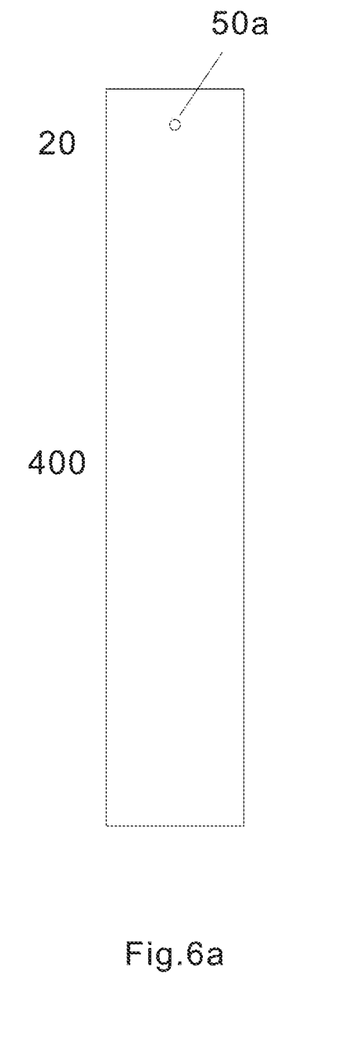
FIG. 6 is a top view of the upper layer to be used in forming a test sensor according to one embodiment.
Figure 6B:
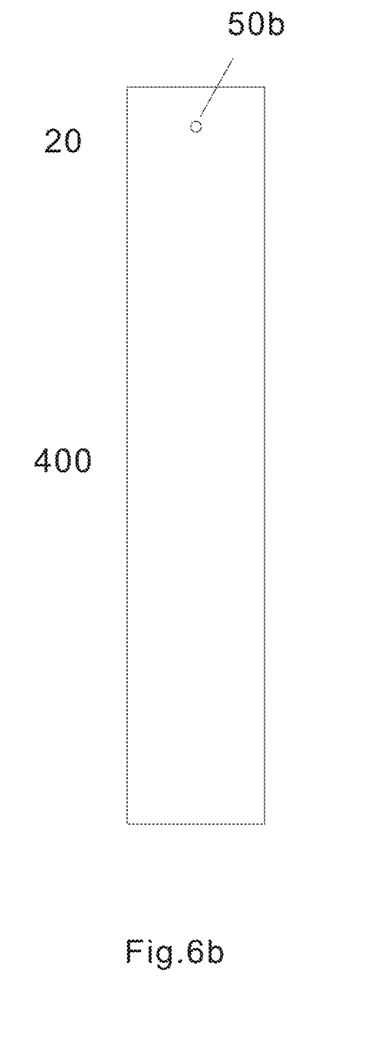

The laminated body may also have an upper layer 400 with a vent opening 50a and 50b, as shown in FIG. 6, bonded to the middle layer 300a and 300b, according to the first and second embodiment, respectively. It virtually has the same width as the base layer 200 and middle layers 300a or 300b, and it has the same length as the middle layer 300a. The upper layer 400 is made of a plastic or polymer materials. Non-limiting examples of polymeric materials, that may be used to form the upper layer 400, include, but not limited to polyethylene, polyethylene terephthalate, polyethylene naphthalate, polyimide and combinations thereof. In one embodiment, the upper layer 400 has a hydrophilic surface facing to the chamber to facilitate the capillary action. It should be understood that the entire side of the upper layer 400 may be coated with a hydrophilic substance and then bonded to the middle layer 300a or 300b. In the present invention, the shape of the vent opening 50a and 50b is not critical at the upper layer 400. In one preferred embodiment, the shape of the vent opening is in round shape.

Figure 7:
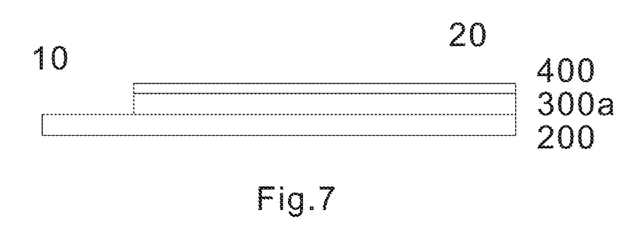
FIG. 7 is a side view of the test sensor according to the first embodiment of the present invention.

FIG. 7 shows side view of the test sensor of the first embodiment consisting of three laminated layers including a base layer 200, middle layer 300a and upper layer 400.

Figure 8:
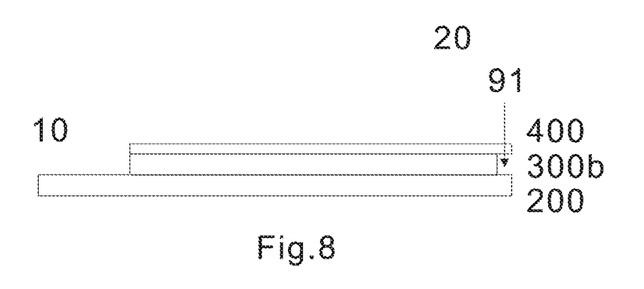
FIG. 8 is a side view of the test sensor according to the second embodiment of the present invention.

FIG. 8 shows side view of the test sensor of the second embodiment consisting of three laminated layers including a base layer 200, middle layer 300b and upper layer 400. Note 91 denotes the side opening described earlier. Its thickness is the same as the middle layer 300b. The length of the side opening 91 is preferably from 0.01 mm to 2.5 mm. More preferably, it is from 0.1 to 0.3 mm. Still more preferably, it is around 0.25 mm. It should be emphasized that the side opening 91 in the unique design of the present invention is just a part of the extra wide sampling opening. The side and front opening combine to form an over 180° sampling angle.

In operation, the fluid sample like blood can enter the thin-layer fluid chamber through any point of the wide opening at the front side of the test sensor according to the first embodiment of the present invention. Thus such unique design allows easily targeting the samples with small volume, picking up smeared samples and alleviating jamming of the opening by users' finger.

The second embodiment in the present invention not only possesses the advantage that the first embodiment does, but it has additional advantage. In the second embodiment, the sampling entrance includes front opening and two side opening 91. The front opening and side opening combine forming a large extra wide sampling entrance, which is over 180°. Thus, blood sample can enter the fluid chamber from any point of the over 180° opening. That is the blood sample can enter from the front opening and can also enter from the side opening 91. Thus such unique design allows even more easily targeting the samples with small volume, picking up smeared samples and alleviating jamming of the opening by users' finger.

By having a test sensor with the extra wide openings in the first embodiment or second embodiment, being adapted to receive a fluid sample, the test sensor of the present invention more easily receives the fluid sample from a user and is more tolerant to users who jam the tip of the sensor into his/her finger, is more tolerant to fluid samples with very small volume (less than 1 microliter) and even smeared samples on the finger tip.

Referring back to FIGS. 2 and 3, the electrode 31, 32, 33 may be loaded with chemistries that react with an analyte to produce detectable electrochemical signals. The chemistries may contain an enzyme, an antibody, an antigen, a complexing reagent, a substrate or combination thereof. The reagents are selected to react with the desired analyte or analytes to be tested so as to assist in determining an analyte concentration of a fluid sample. In one embodiment, the reagents typically contain an enzyme such as, for example, glucose oxidase, glucose dehydrogenase, cholesterol oxidase, creatinine amidinohydrolase, lactate oxidase, peroxidase, uricase, xanthine oxidase and etc. which reacts with the analyte and with an electron acceptor such as a ferricyanide salt to produce an electrochemically measurable species that can be detected by the electrodes. For example, if the analyte of the test sensor is glucose, then glucose oxidase or glucose dehydrogenase may be included as the enzyme; if the analyte of the test sensor is uric acid, then uricase may be included as the enzyme. It should be noted that in some cases more than one enzyme may be included to construct the test sensor in order to generate detectable electrochemical signal. For example, in order to make a test sensor for cholesterol, cholesterol esterase, cholesterol oxidase and peroxidase may be included in the sensor.

In order for the test sensor to work effectively, the electrode 31, 32, 33 may comprise a mixture of a polymer, an enzyme, a surfactant, an electron acceptor, an electron donor, a buffer, a stabilizer and a binder. The electrode 31, 32, 33 may further include a mediator that is an electron acceptor and assists in generating a current that corresponds to the analyte concentration. The preferable mediators could be redox chemicals either in oxidized or reduced form. The mediator used in the present invention may include, but not limited to various metal or noble metal complexes such as potassium ferricyanide, potassium ferrocyanide, cobalt phthalocyanine, various ferrocenes, and various organic redox mediators such as methylene blue, methylene green, 7,7,8,8-tetracyanoquinodimethane, tetrathiafulvalene, toluidine blue, meldola blue, N-methylphenazine methosulfate, phenyldiamines, 3,3',5,5'-tetramethylbenzidine, pyrogallol, and benzoquinone, phenanthroline-5,6-dione and etc. For example, if the enzyme used to construct the test sensor is glucose oxidase or glucose dehydrogenase, then potassium ferricyanide may be included as redox mediator; if the enzyme used to construct the test sensor includes peroxidase, then potassium ferrocyanide may be included as redox mediator.

The electrode 31, 32, 33 include a first working electrode 31, a second working electrode 33 and a reference electrode 32. In one embodiment, the second working electrode 33 serves as a blank electrode without loading a chemistry that reacts with the analyte, such that background signal can be measured and be subtracted from the analyte signal resulted from the first working electrode 31. In this embodiment, effect of interference substances on the analyte signal could be minimized. The background signal may be generated from the matrix of the fluid sample. For example, if the test sensor is used to measure glucose in a blood sample, the background signals may be generated from ascorbic acid, acetaminophen, uric acid, bilirubin and etc. in the blood sample. Still in, this embodiment, the electric signals such as current, impedance at the working electrodes 31 and 33, and time to obtain these signals could be used to estimate filling status of the thin-layer fluid chamber (filled or not). Thus, this embodiment could alert under-fill of fluid samples.

In another embodiment of the present invention, the laminated body of the test sensor has four layers (not shown). Beside the three layers mentioned above, there is an additional middle layer in between the base layer 200 and middle layer 300. This additional middle layer, having at least two cutouts at the sampling end 20, is laminated in between the base layer 200 and middle layer 300. The cutouts at this additional layer not only define the electrode areas and also hold chemical reagents. The cutouts at this additional layer can be accomplished through many methods skilled in the prior arts, such as mechanically drilling, die-cut, laser firing, chemically etching and etc. The shape, size as well as positioning is not critical, but they are within the funnel-like thin-layer fluid chamber. The cutouts can have different shapes, dimensions and/or arrangement orders, without deviating from the scope and spirit of the present invention. The placement of all of the cutouts is such that they will be all positioned within the funnel-like thin-layer fluid chamber described above. The cutouts may be made by die cutting the insulating material mechanically, or cutting with a laser, and then fastening the material to the base layer 200. An adhesive, such as a pressure-sensitive adhesive, may be used to secure this additional middle insulating layer to the base layer 200. Adhesion may also be accomplished by ultrasonically bonding this additional middle insulating layer to the first base layer 200. This additional middle insulating layer may also be made by screen printing an insulating material, by binding a photopolymer or by heat-sealing an insulating material over the base layer 200.

Although the description of test sensor construction above describes construction for a single sensor, the design and materials used can also be used for making multiple sensors from one large piece of each layer material. This would be accomplished by starting with relative large pieces of the base layer material, middle layer material and upper layer material. After a series of preparations described above, a plurality of multiple test sensors thus can be constructed to achieve mass production in a cost-effective way.

It should be noted that although the particular embodiments of the present invention have been described herein, the above description is merely for illustration purpose. Further modification and variations of the invention herein disclosed will occur to those skilled in the respective arts and all such modifications and variations are deemed to be within the scope of the invention as defined by the appended claims.

What is claimed is:

1. An electrochemical test sensor comprising:
   a continuous base layer having a sampling end and an electric contact end, the base layer having electrodes at the sampling end, and electric contacts at the electric contact end, the electrodes being in communication with the electric contacts;
   a middle layer formed of an electrically insulating material having a width approximately equal to a width of the base layer, and having a sampling end and an electric contact end, the middle layer being attached to the base layer, the middle layer forming a cutout region defined by a portion of a front edge being recessed from the middle layer sampling end along the width of the middle layer;
wherein the cutout region is funnel shaped, having inwardly tapering sides;
an upper layer having a sampling end and an electric contact end, the upper layer being attached to the middle layer; and
a fluid chamber defined on a top by the upper layer, on a bottom by the base layer, on a side by the recessed edge of the middle layer defining the cutout region, wherein the cutout region funnel shape extends towards the electric contact end away from the sampling end, the fluid chamber sized and configured to receive a fluid by capillary action, and sized and configured to expose the electrodes of the base layer to the fluid;
wherein the sampling end of the middle layer is slightly recessed from a front edge of the upper layer sampling end and slightly recessed from a front edge of the base layer sampling end, wherein the upper layer, middle layer, and base layer define two side openings in communication with the fluid chamber, a first side opening being on a first side of the sensor at the sampling end, a second side opening being on a second opposite side of the sensor at the sampling end, the two side openings being defined by the middle layer sampling end being slightly recessed from the front edge of the upper layer and base layer sampling ends;
the fluid chamber having a continuous sampling entrance to the fluid chamber defined by an open front opposite to the recessed edge of the middle layer and also defined by the two side openings;
wherein a combined length of the open front and the two side openings of the fluid chamber is less than a perimeter length of the middle layer cutout region; and
wherein the two side openings are configured to allow the fluid to enter the fluid chamber through one of the two side openings when the first or second side is parallel to a surface that the fluid is on.

2. The electrochemical test sensor of claim 1 wherein each of the inwardly tapering sides of the cutout region is formed with a curving inward shape, forming a concave face.

3. The electrochemical test sensor of claim 2 wherein the curving inward shape of each inwardly tapering side is an arc.

4. The electrochemical test sensor of claim 1 wherein the upper layer defines a vent opening through its thickness, the vent positioned over a portion of the fluid chamber, the vent allowing gas to escape from the fluid chamber.

5. The electrochemical test sensor of claim 1 wherein the middle layer is formed of a two-sided adhesive tape.

6. The electrochemical test sensor of claim 1 wherein the upper layer further comprises a hydrophilic material on a surface facing the fluid chamber.

7. The electrochemical test sensor of claim 1 wherein the base layer further comprises a chemistry within the electrodes configured to cause an electrochemical signal once exposed to the fluid within the fluid chamber.

8. The electrochemical test sensor of claim 1 wherein the two side openings immediately exposes and are aligned with a second working electrode, a remainder of the electrodes positioned beneath the middle layer cutout region.

9. The electrochemical test sensor of claim 1 wherein the fluid chamber is adapted to receive a fluid sample of less than one microliter.

10. The electrochemical test sensor of claim 8 wherein the second working electrode exposed by and aligned with the two side openings has no chemistry, and is exposed to fluid before the remainder of the electrodes to establish a background signal before the fluid is exposed to the remainder of the electrodes.

11. The electrochemical test sensor of claim 10 wherein the second working electrode extends to the sampling end of the base layer.

12. The electrochemical test sensor of claim 8 wherein the electrodes are positioned on the base layer such that a fluid flow into the fluid chamber first contacts the second working electrode, then contacts a first working electrode, and then contacts a reference electrode.

13. An electrochemical test sensor comprising:
a base layer having a sampling end and an electric contact end, the base layer having electrodes at the sampling end, and electric contacts at the electric contact end;
a middle layer formed of an electrically insulating material having a width approximately equal to a width of the base layer, and having a sampling end and an electric contact end, the middle layer being attached to the base layer such that a portion of the electric contact end of the base layer extends beyond the electric contact end of the middle layer, while a portion of the base sampling end extends beyond the middle layer sampling end, the middle layer forming a cutout region defined by a recessed front edge portion from the middle layer sampling end;
wherein the cutout region is funnel shaped, having inwardly tapering sides;
an upper layer having a sampling end and an electric contact end, the upper layer being attached to the specified separately for each thread. This can be useful for example for graphicsmiddle layer such that the upper layer sampling end extends slightly beyond the middle layer sampling end, and such that the electric contact end is approximately aligned with the electric contact end of the middle layer;
a fluid chamber defined on a top by the upper layer, on a bottom by the base layer, on a side by the recessed edge of the middle layer defining the cutout region wherein the cutout region funnel shape extends towards the electric contact end away from the sampling end;
wherein the upper layer, middle layer, and base layer define two side openings at the sampling end in communication with the fluid chamber, the two side openings being defined by the upper layer and base layer extending beyond the sampling end of the middle layer, each of the two side openings extending from the front edge corners of the sensor; and
wherein the fluid chamber is sized and configured to receive a fluid by capillary action, and sized and configured to expose the electrodes of the base layer to the fluid;
the fluid chamber having a continuous sampling entrance to the fluid chamber defined by an open front opposite to the recessed edge of the middle layer and also defined by the two side openings;
wherein a combined length of the open front and the two side openings of the fluid chamber is less than a perimeter length of the middle layer cutout region; and
wherein the two side openings are configured to allow the fluid to enter the fluid chamber through one of the two side openings when a first side of the sensor or a second side of the sensor is parallel to a surface that the fluid is on.

14. The electrochemical test sensor of claim 13 wherein each of the inwardly tapering sides of the cutout region is formed with a curving inward shape, forming a concave face.

15. The electrochemical test sensor of claim 14 wherein the curving inward shape of each inwardly tapering side is an arc.

16. The electrochemical test sensor of claim 13 wherein the upper layer defines a vent opening through its thickness, the vent positioned at the top of the fluid chamber.

17. The electrochemical test sensor of claim 13 wherein the middle layer is formed of a two-sided adhesive tape.

18. The electrochemical test sensor of claim 13 wherein the upper layer further comprises a hydrophilic material on a surface facing the fluid chamber.

* * * * *